United States Patent [19]

Gilkerson et al.

[11] Patent Number: 5,152,825
[45] Date of Patent: Oct. 6, 1992

[54] HERBICIDAL 2-PYRIDYLOXY-BENZOYL-ACRYLONITRILES

[75] Inventors: Terence Gilkerson, Canterbury; Robert W. Shaw, Sittingbourne, both of England

[73] Assignee: Shell International Research Maatschappij B.V., The Hague, Netherlands

[21] Appl. No.: 588,933

[22] Filed: Sep. 27, 1990

Related U.S. Application Data

[62] Division of Ser. No. 357,276, May 26, 1989, Pat. No. 4,988,385.

[30] Foreign Application Priority Data

Jun. 22, 1988 [GB] United Kingdom ............... 8814881

[51] Int. Cl.⁵ ............... C07D 213/643; C07D 213/84; C07D 213/71; A01N 43/40
[52] U.S. Cl. ...................................... 71/94; 546/288; 546/294; 546/296; 546/297; 546/300
[58] Field of Search ............... 546/300, 288, 294, 296, 546/297; 71/94

[56] References Cited

U.S. PATENT DOCUMENTS 3,865,863 2/1975 Field ................................. 558/405
4,596,883 6/1986 Schwindeman ..................... 558/405
4,699,992 10/1987 Grohe ................................ 558/405

FOREIGN PATENT DOCUMENTS 129846 1/1985 European Pat. Off. ............ 558/405

*Primary Examiner*—Alan L. Rotman

[57] ABSTRACT

Compounds of the general formula

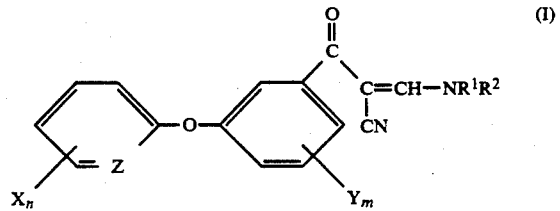

in which $R^1$ and $R^2$ each independently represents an alkyl group, Z represents a nitrogen atom or a group CH unsubstituted or substituted by a substituent X, m is 0 or an integer from 1 to 4, the or each Y represents a halogen atom, n is 0 or an integer from 1 to 5, and the or each X represents a halogen atom or a group selected from alkyl, haloalkyl, cyanoalkyl, alkenyl, alkynyl, alkoxy, alkenyloxy, alkynyloxy, alkylthio, alkenylthio, alkynylthio, cyano, nitro, alkylsulphonyl, alkylsulphinyl, and sulphonamido, have been found to have herbicidal activity.

14 Claims, No Drawings

HERBICIDAL 2-PYRIDYLOXY-BENZOYL-ACRYLONITRILES

This is a divisional of copending application(s) Ser. No. 07/357,276 filed May 26, 1989 now U.S. Pat. No. 4,988,385.

This invention relates to certain new herbicidal acrylonitrile derivatives, their preparation, herbicidal compositions containing such derivatives and to a method of combating undesired plant growth using such derivatives and compositions.

The preparation and herbicidal use of certain acrylonitrile derivatives has been described in German OLS 2 330 913. Such acrylonitriles have an α-carbonyl linkage with a substituent selected from optionally substituted phenyl, naphthyl, thienyl and furyl groups, the optional substituents being restricted to halogen, nitro, alkoxy and alkyl.

The present invention relates to a new class of herbicidal aryl- or heteroaryl-oxybenzoylacryl-onitrile derivatives.

Accordingly, the present invention provides a compound of the general formula I

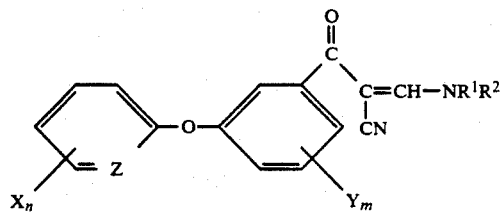

in which $R^1$ and $R^2$ each independently represents an alkyl group, Z represents a nitrogen atom or a group CH which is unsubstituted or substituted by a substituent X, m is 0 or an integer from 1 to 4, the or each Y independently represents a halogen atom, n is 0 or an integer from 1 to 5, and the or each X independently represents a halogen atom or a group selected from alkyl, haloalkyl, cyanoalkyl, alkenyl, alkynyl, alkoxy, alkenyloxy, alkynyloxy, alkylthio, alkenylthio, alkynylthio, cyano, nitro, alkylsulphonyl, alkylsulphinyl and sulphonamido.

As used herein the term alkyl, alkenyl or alkynyl in respect of a radical or moiety refers to a straight or branched chain radical or moiety. Suitably an alkyl radical or moiety has from 1 to 12 carbon atoms, preferably from 1 to 6 and especially from 1 to 4 carbon atoms. Alkenyl and alkynyl radicals or moieties suitably have from 2 to 12 carbon atoms, preferably from 2 to 6, especially from 2 to 4, carbon atoms.

Preferably $R^1$ and $R^2$ each independently represents an alkyl group of 1 to 4 carbon atoms: and most preferably $R^1$ and $R^2$ are the same and each represents a methyl group.

Z preferably represents an unsubstituted group CH, the compound of general formula I then being a diphenyl ether derivative.

When m is greater than 1, the substituents Y may be the same or different and may suitably be selected from chlorine, bromine and fluorine atoms. Preferably either m is 0 or m is 1 and Y represents a chlorine atom.

When n is greater than 1, the substituents X may be the same or different and may suitably be selected from halogen atoms, especially fluorine, chlorine and bromine atoms, $C_{1-6}$ alkyl groups, $C_{1-6}$ haloalkyl groups, $C_{1-6}$ cyanoalkyl, $C_{1-6}$ alkoxy groups, $C_{1-6}$ alkylthio groups, $C_{1-6}$ alkylsulphinyl groups, $C_{1-6}$ alkylsulphonyl groups, cyano groups and nitro groups. Preferably n is 1 or 2 and the or each substituent X independently represents a fluorine atom, a chlorine atom, a bromine atom, a $C_{1-4}$ alkyl group, a $C_{1-4}$ haloalkyl group, especially trifluoromethyl, a $C_{1-4}$ cyanoalkyl group, especially cyanomethyl, a $C_{1-4}$ alkoxy group, especially methoxy, a $C_{1-4}$ alkylthio group, especially methylthio, a $C_{1-4}$ alkylsulphinyl group, especially methylsulphinyl, a $C_{1-4}$ alkylsulphonyl group, especially methylsulphonyl, a cyano group or a nitro group.

The compounds of general formula I may either be prepared from a corresponding diphenyl ether or pyridyl phenyl ether derivative by reaction in one or more steps to introduce the dialkylaminoacrylonitrile moiety, or be prepared by introducing a suitable phenyl or pyridyl moiety into an appropriate benzoyldialkylamino acrylonitrile derivative.

According to a further aspect of the invention, we therefore provide a process for the preparation of a compound of general formula I, which comprises reacting a compound of general formula II

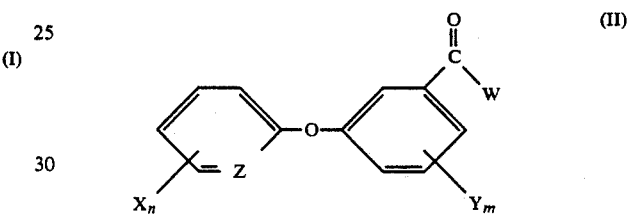

wherein X, Y, Z, n and m are as defined above and W represents a halogen atom or a cyanomethyl group, with, in the case where W is halogen, a dialkylaminoacrylonitrile under basic conditions, or, in the case where W is cyanomethyl, either with a dialkylformamide dialkyl acetal or with a trialkylorthoformate followed by reaction with a dialkylamine, or reacting a compound of general formula III

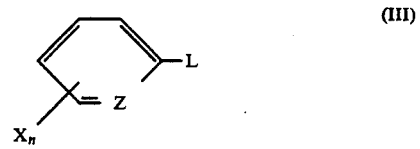

wherein n, X and Z are as hereinbefore defined and L represents a leaving group
with a compound of general formula IV

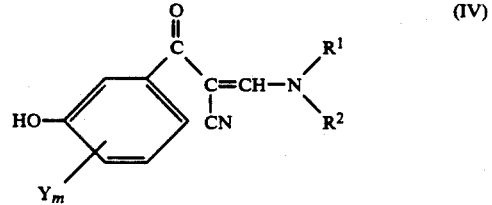

wherein m, Y, $R^1$ and $R^2$ are as hereinbefore defined, under basic conditions, and, if desired or required, converting a resulting compound of general formula I into another of general formula I.

When W in a compound of general formula II represents a cyanomethyl group, the reaction to form the compound of formula I is carried out using a dialkylformamide dialkyl acetal, preferably dimethyl formamide dimethyl acetal. Suitably the reaction is carried out in the presence of an inert organic solvent, suitable solvents being halogenated hydrocarbons, for example dichloromethane, ethers, such as diethyl ether, or esters, such as ethyl acetate; mixtures of solvents may also be utilised. Preferably the reaction is carried out at a temperature in the range of from 0° to 50° C., suitably at ambient temperature.

Alternatively, when W in a compound of general formula II represents a cyanomethyl group, the reaction may be carried out in a two stage procedure by reacting the cyanomethyl carbonyl compound II with a trialkylorthoformate, preferably trimethylorthoformate, followed, optionally after isolation of the alkoxyaroyl acrylonitrile so formed, by reaction with excess dialkylamine, preferably dimethylamine in a suitable solvent. Suitable solvents are, for example, halogenated hydrocarbons, such as dichloromethane, alcohols, such as ethanol, ethers such as diethyl ether, and esters; mixtures of solvents are also suitable. The reaction may be carried out at a temperature in the range of from −10° to 100° C. Preferably the first stage is carried out at elevated temperature, for example at a temperature in the range of from 60° to 100° C., suitably at approximately 80° C., while the second stage is carried out at a lower temperature, suitably a temperature below 60° C. and conveniently ambient temperature. Preferably the reaction is carried out without isolation of the intermediate acrylonitrile.

When W in a compound of general formula II represents a halogen atom, preferably chlorine, the compound of formula II is reacted with a dialkylaminoacrylonitrile, preferably dimethylaminoacrylonitrile preferably in the presence of a solvent, for example an ether solvent, and in the presence of a base, for example a tertiary amine. A preferred ether solvent is dioxan and a preferred tertiary amine base is triethylamine. The reaction is preferably carried out at a temperature in the range of from 50° to 120° C., conveniently at the reflux temperature of the solvent employed.

Compounds of the general formula I may also be prepared by reacting a compound of general formula III with a compound of general formula IV. Preferably the reaction is carried out under basic conditions and in the presence of a suitable solvent. Suitably the reaction is carried out in the presence of an alkali metal or alkaline earth metal carbonate, for example potassium carbonate. Suitable solvents are organic solvents that are inert to the reaction media and conveniently may be, for example, dimethyl formamide; again mixtures of solvents may be used. Preferably the reaction is carried out under anhydrous conditions. The reaction may conveniently be effected at a temperature in the range of from 0 to the reflux temperature of the reaction mixture, but is preferably carried out at reflux.

A leaving group represented by L may be any group that will, under the reaction conditions, cleave from the reactant III thus promoting reaction at a specified site. The group L in a compound of general formula III is suitably a halogen atom, preferably chlorine or fluorine.

Following either method of preparation the resulting compound of general formula I may be isolated and purified using conventional techniques, for example by solvent extraction, evaporation and recrystallisation or by chromatography on silica.

Compounds of general formula II are believed to be novel intermediates and the present invention further includes such compounds and their preparation.

Compounds of general formula II in which W represents a cyanomethyl group may be prepared from the alkyl ester of the corresponding diaryl or aryl heteroaryl ether. Thus the invention further provides a process for the preparation of a compound of formula II as defined above which comprises reacting a compound of formula V:

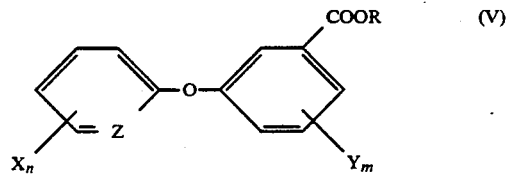

Wherein X, Y, Z, n and m are as defined above and R represents an alkyl group, with acetonitrile under basic conditions.

Preferably the basic conditions are provided by an alkali metal amide, such as sodamide or potassium amide, suitably in liquid ammonia, or sodium or potassium hydride in a solvent such as dimethylformamide. Alternatively the basic conditions may be provided by an alkoxide such as sodium or potassium methoxide with excess acetonitrile as solvent. Suitable temperatures for the reaction are in the range of from −70° C. to 100° C. and are usually determined by the basic conditions employed.

Compounds of formula V may be prepared by esterification of the corresponding acid with an alcohol, such as methanol, in the presence of an acidic catalyst, for example concentrated sulphuric acid, dry hydrogen chloride gas or p-toluene sulphonic acid. The reactant acids may suitably be prepared by oxidation of the corresponding diaryl/aryl heteroaryl ether aldehyde using, for example, chromium trioxide in the presence of acetic acid or, more preferably, sulphuric acid in an inert solvent such an aromatic solvent, eg. benzene, or a ketone, eg. acetone, or manganese dioxide in an inert solvent such as a halogenated hydrocarbon, e.g. dichloromethane, an ester, eg. ethyl acetate, or a ketone. Suitable temperatures are in the range of from −20° to 50° C., preferably −5° to 20° C. The ether aldehydes may themselves conveniently be prepared by condensation of an optionally substituted phenol and a m-halobenzaldehyde, for example in the presence of an alkali metal alkoxide, such as sodium methoxide, followed by treatment with a copper catalyst such as cuprous chloride in pyridine and an aromatic hydrocarbon, such as xylene; as described in U.K. patent specification no. 2050168. The reaction may alternatively be carried out in the presence of an alkali metal carbonate, for example sodium or potassium carbonate, followed by treatment with cuprous oxide and/or copper powder in dimethylformamide or quinoline. The reaction may suitably be carried out at a temperature in the range of from 20° to 150° C. and conveniently the reaction is carried out at the reflux temperature of the reaction mixture.

Alternatively, the compounds of general formula V may be prepared by condensation of an optionally substituted phenol with a meta-halobenzoic acid ester, suitably using conditions similar to those described above for the preparation of the diaryl/aryl heteroaryl ether aldehydes.

Compounds of general formula II in which W represents a halogen atom may be derived from the corresponding ether carboxylic acid, for example by reaction of the acid with thionyl chloride. The acid may be derived as described above from a phenolic compound and a m-halobenzaldehyde or m-halobenzoic acid ester.

Compounds of general formula III are known compounds and may be prepared using conventional techniques.

The compounds of general formula IV are believed to be novel and may be prepared by reacting a compound of general formula VI

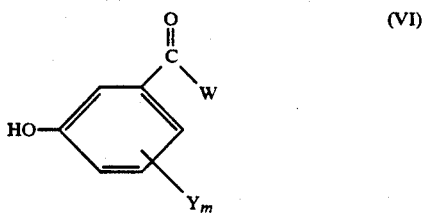

in which $Y_m$ is as defined above and W represents a cyanomethyl group,
with a dialkylformamide dialkyl acetal, preferably dimethylformamide dimethylacetal, under the same conditions as described above for the reaction of compounds of general formula II in which W is a cyanomethyl group, with a dialkylformamide dialkyl acetal.

The compounds of the invention have been found to have surprisingly high herbicidal activity with a wide spectrum of activity against broadleaved weeds and grasses especially when applied post-emergence.

Accordingly, the invention further provides a herbicidal composition comprising a compound of formula I as defined above in association with at least one carrier, and a method of making such a composition which comprises bringing a compound of formula I into association with at least one carrier.

The invention also provides the use of such a compound or composition according to the invention as a herbicide. Further, in accordance with the invention there is provided a method of combating undesired plant growth at a locus by treating the locus with a compound or composition according to the invention. Application to the locus may be pre-emergence or post-emergence, preferably post-emergence. The dosage of active ingredient used may, for example, be in the range of from 0.01 to 10 kg/ha, suitably 0.05 to 4 kg/ha. The locus may, for example, be the soil or plants in a crop area, typical crops being cereals such as wheat, barley and rice.

A carrier in a composition according to the invention is any material with which the active ingredient is formulated to facilitate application to the locus to be treated, which may for example be a plant, seed or soil, or to facilitate storage, transport or handling. A carrier may be a solid or a liquid, including a material which is normally gaseous but which has been compressed to form a liquid, and any of the carriers normally used in formulating herbicidal compositions may be used. Preferably compositions according to the invention contain 0.5 to 95% by weight of active ingredient.

Suitable solid carriers include natural and synthetic clays and silicates, for example natural silicas such as diatomaceous earths; magnesium silicates, for example talcs; magnesium aluminium silicates, for example attapulgites and vermiculites; aluminium silicates, for example kaolinites, montmorillonites and micas; calcium carbonate; calcium sulphate; ammonium sulphate; synthetic hydrated silicon oxides and synthetic calcium or aluminium silicates; elements, for example carbon and sulphur; natural and synthetic resins, for example coumarone resins, polyvinyl chloride, and styrene polymers and copolymers; solid polychlorophenols; bitumen; waxes; and solid fertilisers, for example superphosphates.

Suitable liquid carriers include water; alcohols, for example isopropanol and glycols; ketones, for example acetone, methyl ethyl ketone, methyl isobutyl ketone and cyclohexanone; ethers; aromatic or araliphatic hydrocarbons, for example benzene, toluene and xylene; petroleum fractions, for example kerosine and light mineral oils; chlorinated hydrocarbons, for example carbon tetrachloride, perchloroethylene and trichloroethane. Mixtures of different liquids are often suitable.

Agricultural compositions are often formulated and transported in a concentrated form which is subsequently diluted by the user before application. The presence of small amounts of a carrier which is a surface-active agent facilitates this process of dilution. Thus preferably at least one carrier in a composition according to the invention is a surface-active agent. For example the composition may contain at least two carriers, at least one of which is a surface-active agent.

A surface-active agent may be an emulsifying agent, a dispersing agent or a wetting agent; it may be nonionic or ionic. Examples of suitable surface-active agents include the sodium or calcium salts of polyacrylic acids and lignin sulphonic acids; the condensation of fatty acids or aliphatic amines or amides containing at least 12 carbon atoms in the molecule with ethylene oxide and/or propylene oxide; fatty acid esters of glycerol, sorbitol, sucrose or pentaerythritol; condensates of these with ethylene oxide and/or propylene oxide; condensation products of fatty alcohol or alkyl phenols, for example p-octylphenol or p-octylcresol, with ethylene oxide and/or propylene oxide; sulphates or sulphonates of these condensation products; alkali or alkaline earth metal salts, preferably sodium salts, of sulphuric or sulphonic acid esters containing at least 10 carbon atoms in the molecule, for example sodium lauryl sulphate, sodium secondary alkyl sulphates, sodium salts of sulphonated castor oil, and sodium alkylaryl sulphonates such as dodecylbenzene sulphonate; and polymers of ethylene oxide and copolymers of ethylene oxide and propylene oxide.

The compositions of the invention may for example be formulated as wettable powders, dusts, granules, solutions, emulsifiable concentrates, emulsions, suspension concentrates and aerosols. Wettable powders usually contain 25, 50 or 75% w of active ingredient and usually contain in addition to solid inert carrier, 3–10% w of a dispersing agent and, where necessary, 0–10% w of stabiliser(s) and/or other additives such as penetrants or stickers. Dusts are usually formulated as a dust concentrate having a similar composition to that of a wettable powder but without a dispersant, and are diluted in the field with further solid carrier to give a composition usually containing ½–10% w of active ingredient. Granules are usually prepared to have a size between 10 and 100 BS mesh (1.676–0.152 mm), and may be manufactured by agglomeration or impregnation techniques. Generally, granules will contain ½–75% w active ingredient and 0–10% w of additives such as stabilisers, surfactants, slow release modifiers and binding agents. The so-called "dry flowable powders" consist of relatively small granules having a relatively high concentration of active ingredient. Emulsifiable concentrates usually contain, in addition to a solvent and, when necessary, co-solvent, 10–50% w/v active ingredient, 2–20% w/v emulsifiers and 0–20% w/v of other additives such as stabilisers, penetrants and corrosion inhibitors. Suspension concentrates are usually compounded so as to obtain a stable, non-sedimenting flowable product and usually contain 10–75% w active ingredient, 0.5–15% w of dispersing agents, 0.1–10% w of suspending agents such as protective colloids and thixotropic agents, 0–10% w of other additives such as defoamers, corrosion inhibitors, stabilisers, penetrants and stickers, and water or an organic liquid in which the active ingredient is substantially insoluble; certain organic solids or inorganic salts may be present dissolved in the formulation to assist in preventing sedimentation or as antifreeze agents for water.

Aqueous dispersions and emulsions, for example compositions obtained by diluting a wettable powder or a concentrate according to the invention with water, also lie within the scope of the invention. The said emulsions may be of the water-in-oil or of the oil-in-water type, and may have a thick 'mayonnaise'-like consistency.

The composition of the invention may also contain other ingredients, for example other compounds possessing herbicidal, insecticidal or fungicidal properties.

The following Examples illustrate the invention, Examples 1 to 5 relate to the preparation of starting materials, Examples 6 to 44 to the preparation of novel intermediates of general formula II and Examples 45 to 91 to the preparation of compounds of general formula I.

All structures were confirmed by mass spectroscopy and 300'H nmr.

EXAMPLE 1

Preparation of 3-(3'- $\alpha$, $\alpha$,$\alpha$-trifluoromethylphenoxy)benzaldehyde A solution of sodium (2.65 g) in methanol (45 ml) was added to a stirred solution of 3-( $\alpha$, $\alpha$, $\alpha$-tri-fluoromethyl)phenol (17.8 g) in xylene (125 ml) under a nitrogen atmosphere. The mixture was heated to reflux and xylene distilled out, with continuous replacement by fresh, dry xylene until the total distillate was 200 ml. The mixture was cooled, cuprous chloride (3.0 g) and pyridine (50 ml) were added and the mixture heated to reflux. A solution of 3-bromobenzaldehyde (18.5 g) in xylene (25 ml) was added dropwise and the mixture refluxed for 10 hours. After cooling, the mixture was poured into water (250 ml) and acidified with dilute hydrochloric acid. The aqueous solution was extracted with diethyl ether. The ethereal extracts were washed with aqueous sodium hydrogen carbonate and brine and dried over anhydrous MgSO$_4$. After filtration and evaporation, the residual liquid was chromatographed on a silica gel column to give 3-(3'-$\alpha$, $\alpha$, $\alpha$-trifluoromethylphenoxy)benzaldehyde as a colourless oil (9 g, 34%)

| Analysis | | |
|---|---|---|
| Calculated for C$_{14}$H$_9$O$_2$F$_3$: | C 63.2; | H 3.4% |
| Found | C 63.6; | H 3.5% |

EXAMPLE 2

Preparation of 3-(3'- $\alpha$, $\alpha$, $\alpha$-trifluoromethylphenoxy) benzoic acid A solution of oxidation mixture (45 ml), (derived from 41.2 g CrO$_3$ in 120 ml water and 35 ml concentrated sulphuric acid) was added to a solution of 3-(3'-$\alpha$, $\alpha$, $\alpha$-trifluoromethylphenoxy) benzaldehyde (24.3 g) in acetone (50 ml), keeping the temperature below 25° C. After stirring at room temperature for 1 hour, ice-water (500 g) was added and the white solid filtered off to give the title product (25 g, 97%) of m.p. 109°–110° C.

| Analysis: | | |
|---|---|---|
| Calculated for C$_{14}$H$_9$O$_3$F$_3$: | C 59.6; | H 3.2% |
| Found | C 59.9; | H 3.3% |

EXAMPLE 3

Preparation of Methyl-3-(3'- $\alpha$, $\alpha$, $\alpha$-trifluoromethylphenoxy)benzoate A solution of 3-(3'-$\alpha$, $\alpha$, $\alpha$-trifluoromethylphenoxy)benzoic acid (23 g) in methanol (200 ml) with concentrated H$_2$SO$_4$ (0.5 ml) was refluxed for 6 hours. The methanol was evaporated in vacuo and the residue dissolved in diethyl ether. The ethereal solution was washed with aqueous NaHCO$_3$ and brine, dried over anhydrous MgSO$_4$, filtered and evaporated to give the title ester (22 g, 91%) as a yellow oil.

| Analysis: | | |
|---|---|---|
| Calculated for C$_{15}$H$_{11}$O$_3$F$_3$: | C 60.8; | H 3.7% |
| Found | C 61.6; | H 4.0% |

EXAMPLE 4

Preparation of Ethyl-3-(4'-fluorophenoxy) benzoate

A solution of sodium methoxide (from 2.65 g sodium and 45 ml of methanol) was added to a solution of 4-fluorophenol (12.3 g) in xylene (100 ml). The resulting solution was evaporated to dryness in vacuo. Fresh xylene (100 ml) was added to the sodium phenolate and the xylene re-evaporated. Pyridine (50 ml) and xylene (100 ml) were added to the dry sodium phenolate, followed by cuprous chloride (3 g). The solution was heated to reflux with stirring and a solution of 3-bromobenzoate (22.9 g) in xylene (25 ml) was added dropwise. The resultant mixture was refluxed a further 6 hours. After cooling, the reaction mixture was poured into water, acidified with dilute HCl and the aqueous phase extracted with diethyl ether. After drying over anhydrous magnesium sulphate, the ether was evaporated. The residual oil was purified on a silica gel column using methylene chloride as eluant to give the title compound (21 g) as a pale yellow oil.

| Analysis: | | |
|---|---|---|
| Calculated for C$_{15}$H$_{13}$O$_3$F: | C 69.2; | H 5.0% |
| Found: | C 68.5; | H 4.8% |

EXAMPLE 5

Preparation of Methyl-3-(5'-α, α, α-trifluoromethyl-2-pyridyloxy)benzoate

Methyl-3-hydroxybenzoate (9.1g) in dry dimethylformamide (20 ml) is added dropwise to a suspension of sodium hydride (2.6 g of 60% dispersion in oil) in dry dimethyl formamide (60 ml), the temperature being maintained below 20° C. After stirring for a further 30 minutes, 2-chloro-5-α, α, α-trifluoromethyl) pyridine (10.9 g) in dry dimethyl formamide (20 ml) was added dropwise and the resulting solution stirred overnight at room temperature. The reaction mixture was then poured into water and the product extracted with diethyl ether. The ethereal extracts were dried over $MgSO_4$, filtered and evaporated. The residual oil was chromatographed on a silica gel column using dichloromethane as eluant to give the title compound as a colourless oil (11.5 g, 65%).

| Analysis: | | | |
|---|---|---|---|
| Calculated for $C_{14}H_{10}NO_3F_3$: | C 56.5; | H 3.4; | N 4.7% |
| Found: | C 56.0; | H 3.6; | N 5.1% |

EXAMPLE 6

Preparation of 3-(3'-α, α, α-trifluoromethylphenoxy)benzoyl acetonitrile

To a suspension of sodamide (prepared from 1.2 g sodium metal in 60 ml of liquid ammonia) was added a solution of dry acetonitrile (2.1g) in dry diethylether (5 ml) over 5 minutes. After a further 5 minutes methyl-3-(3'-α, α, α-trifluoromethyl)phenoxy)benzoate (7.4 g) was added as quickly as possible. After stirring for a further 1 hour at a temperature between −30° to −15° C., the ammonia was removed by warming on a water bath, whilst at the same time, diethyl ether was added to maintain the reaction flask volume of approximately 100 ml. The ethereal solution was then cautiously poured onto ice (50 g). The aqueous layer was separated, washed with ether and acidified with 6N HCl. Purification of the filtered solid on a silica gel column using 5% v/v diethyl ether/dichloromethane as eluant gave the title compound (5 g, 66%) as a white solid of m.p. 0°-61° C.

| Analysis: | | | |
|---|---|---|---|
| Calculated for $C_{16}H_{10}O_2NF_3$: | C 62.9; | H 3.3; | N 4.6% |

| Analysis: | | | |
|---|---|---|---|
| Found: | C 63.0; | H 3.3; | N 4.8% |

EXAMPLE 7

Preparation of 3-phenoxybenzoylacetonitrile

A solution of sodium methoxide (from 1.2 g sodium in 25 ml methanol) was added dropwise over 2 hours to a refluxing solution of methyl-3-phenoxybenzoate (11 g) in acetonitrile (100 ml) under a nitrogen atmosphere while distilling off methanol and excess acetonitrile. After complete removal of methanol the reaction mixture was poured onto ice-water (200 g) and acidified with 50% HCl. The solid was filtered off and dried to give the title compound (7.5 g, 65%) as a white solid of m.p. 95°-96° C.

| Analysis: | | | |
|---|---|---|---|
| Calculated for $C_{15}H_{11}O_2N$: | C 75.9; | H 4.6; | N 5.9% |
| Found: | C 75.7; | H 4.7; | N 5.9% |

EXAMPLE 8

Preparation of 3-(5'-α, α, α-trifluoromethyl-2-pyridyloxy)benzoylacetonitrile

Dry acetonitrile (2.8 g) was added to a stirred suspension of sodium hydride (2.7 g of 60% dispersion in oil) in dry dimethyl formamide (50 ml). The mixture was heated to 60° C. for 1 hour. Methyl-3-(5'-α, α, α-trifluoromethyl-2-pyridyloxy)benzoate (10 g) was added and the reaction mixture left to cool and stirred at room temperature overnight. The mixture was poured onto ice and the product extracted with diethyl ether. The aqueous phase was acidified with dilute HCl and extracted with diethyl ether. The ethereal extracts were dried over $MgSO_4$, filtered and evaporated. The residual oil was chromatographed on a silica gel column using dichloromethane as eluant to give the title compuond (4.8 g, 47%) as a white solid of m.p. 85°-86° C.

| Analysis: | | | |
|---|---|---|---|
| Calculated for $C_{15}H_9N_2O_2F_3$: | C 58.8; | H 2.9; | N 9.2% |
| Found: | C 58.5; | H 2.9; | N 9.0% |

The compounds of general formula II listed in Table 1 below, were prepared by methods similar to those described in Examples 6,7 and 8 above.

TABLE 1

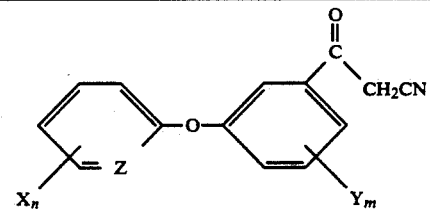

| Example No. | Xn | Z | Ym | C (Calc. Found) | H (Calc. Found) | N (Calc. Found) | Melting Point (°C.) |
|---|---|---|---|---|---|---|---|
| 9 | 2-Cl, 4-$CF_3$ | CH | — | 56.5 55.5 | 2.6 2.7 | 4.1 4.0 | not recorded |

TABLE 1-continued
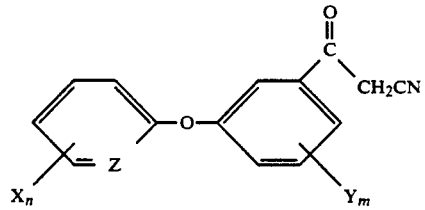
| Example No. | Xn | Z | Ym | C (Calc. Found) | H (Calc. Found) | N (Calc. Found) | Melting Point (°C.) |
|---|---|---|---|---|---|---|---|
| 10 | 4-Cl | CH | — | 66.3 66.6 | 3.7 3.9 | 5.2 5.7 | 96–97 |
| 11 | 4-CH$_3$ | CH | — | 76.5 76.3 | 5.2 5.2 | 5.6 5.7 | 77–78 |
| 12 | 3,5-diCl | CH | — | 58.8 58.5 | 2.9 3.1 | 4.5 4.1 | 123–124 |
| 13 | 4-OCH$_3$ | CH | — | 71.9 72.2 | 4.9 4.8 | 5.2 5.4 | 78–79 |
| 14 | 3,4-diCl | CH | — | 58.8 59.1 | 2.9 3.0 | 4.6 4.6 | 99–100 |
| 15 | 4-isopropyl | CH | — | 77.4 77.1 | 6.1 6.0 | 5.0 5.3 | 77–79 |
| 16 | 2,4-diCH$_3$ | CH | — | 77.0 76.5 | 5.7 5.6 | 5.3 5.6 | 116–117 |
| 17 | 5-Cl | N | — | 61.8 61.6 | 3.3 3.3 | 10.3 10.3 | 106–107 |
| 18 | 2-CH$_3$ | CH | — | 76.5 73.3 | 5.2 4.9 | 5.6 6.0 | 55–57 |
| 19 | 4-SCH$_3$ | CH | — | 67.8 67.4 | 4.6 4.6 | 4.9 5.0 | 103–104 |
| 20 | 2,4-diCl | CH | — | 58.8 58.3 | 2.9 3.0 | 4.6 4.8 | 102–104 |
| 21 | 4-F | CH | — | 70.6 70.3 | 3.9 4.0 | 5.5 5.9 | 104–105 |
| 22 | 3,4-diF | CH | — | 65.9 65.5 | 3.3 3.3 | 5.1 5.7 | 89–90 |
| 23 | 2,5-diCH$_3$ | CH | — | 77.0 77.5 | 5.7 5.8 | 5.3 5.3 | 109–110 |
| 24 | 2-F | CH | — | 70.6 70.1 | 3.9 3.2 | 5.5 5.8 | 60–64 |
| 25 | 3-F | CH | — | 70.6 67.0 | 3.9 3.8 | 5.5 5.9 | 62–64 |
| 26 | 4-CN | CH | — | 73.3 72.8 | 3.8 3.8 | 10.7 10.7 | 127–129 |
| 27 | 3-Cl | N | — | 61.7 61.7 | 3.3 3.6 | 10.3 10.2 | 129–130 |
| 28 | 5-Br | N | — | 53.0 52.8 | 2.8 2.9 | 8.8 8.9 | 118–119 |
| 29 | 3-CF$_3$, 4-Cl | CH | — | 56.6 56.6 | 2.7 2.8 | 4.1 4.2 | 99–101 |
| 30 | 4-C$_2$H$_5$ | CH | — | 77.0 77.9 | 5.7 5.3 | 5.3 5.9 | 67–69 |
| 31 | 4-Br | CH | — | 57.0 56.5 | 3.2 3.2 | 4.4 4.4 | 101–103 |
| 32 | 4-tC$_4$H$_9$ | CH | — | 77.8 71.3 | 6.5 6.0 | 4.8 4.8 | oil |
| 33 | 4-secC$_4$H$_9$ | CH | — | 77.8 74.4 | 6.5 6.4 | 4.8 4.4 | oil |
| 34 | 2-CH$_3$, 4-Cl | CH | — | 67.4 66.2 | 4.2 4.0 | 4.9 4.7 | 125–126 |
| 35 | 3-CF$_3$, 4-F | CH | — | 59.4 59.0 | 2.8 3.2 | 4.3 4.6 | 68–70 |
| 36 | 2-Cl | CH | — | 66.4 64.9 | 3.7 3.9 | 5.2 5.0 | 50–51 |
| 37 | 3-CH$_3$, 4-Cl | CH | — | 67.4 67.5 | 4.2 4.2 | 4.9 4.6 | 89–90 |
| 38 | 3-Cl | CH | — | 66.4 66.1 | 3.7 3.8 | 5.2 5.4 | 87–88 |
| 39 | 3-OCH$_3$ | CH | — | 71.9 71.4 | 4.9 4.9 | 5.2 5.4 | 55–56 |
| 40 | 2,4-diF | CH | — | 65.9 64.9 | 3.3 3.2 | 5.1 5.0 | oil |
| 41 | 2-Cl, 4-F | CH | — | 62.3 61.9 | 3.1 3.2 | 4.8 5.1 | 95–96 |
| 42 | 3,5-diCH$_3$ | CH | — | 77.0 76.9 | 5.7 5.7 | 5.3 5.7 | 75–76 |
| 43 | 3-CF$_3$ | CH | 5-Cl | 56.6 | 2.6 | 4.1 | oil |

TABLE 1-continued

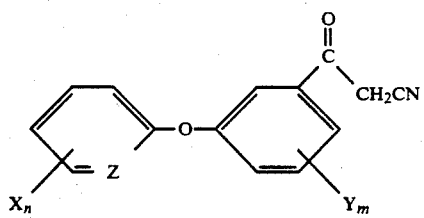

| Example No. | $X_n$ | Z | $Y_m$ | C (Calc. Found) | H (Calc. Found) | N (Calc. Found) | Melting Point (°C.) |
|---|---|---|---|---|---|---|---|
| 44 | 3-CH$_2$CN, 5-CF$_3$ | N | — | 55.7 59.1 59.0 | 2.7 2.9 3.1 | 4.0 12.2 12.0 | not recorded |

EXAMPLE 45

Preparation of 2-[3-(3'-α, α, α-trifluoromethylphenoxy)benzoyl]-3-dimethylaminoacrylonitrile To a solution of 3-(3'-α, α, α-trifluoromethylphenoxy)benzoyl acetonitrile (3 g) in dichloromethane (50 ml) was added dimethylformamide dimethylacetal (6 ml). After stirring overnight at room temperature, the dichloromethane was evaporated. The residue was purified on a silica gel column using 5% methanoldichloromethane (v/v) as eluant to give the title compound (3 g, 85%) as a white solid of m.p. 84°–85° C.

| Analysis: | | | |
|---|---|---|---|
| Calculated for C$_{19}$H$_{15}$N$_2$O$_2$F$_3$: | C 63.3; | H 4.2; | N 7.8% |
| Found: | C 63.4; | H 4.5; | N 7.8% |

EXAMPLE 46

Preparation of 2-(3-phenoxybenzoyl)-3-dimethylaminoacrylonitrile

3-Phenoxybenzoylacetonitrile (4 g) and trimethylorthoformate (30 ml) was stirred and heated to 80° C. for 2 hours. After cooling to 0° C., an excess of dimethylamine in ethanol solution was added and the mixture stirred for 2 hours at room temperature. The volatiles were then removed in vacuo and the residue chromatographed on a silica gel column using 5% methanoldichloromethane (v/v) as eluant to give the title compound (3.2 g, 65%) as a white solid of m.p. 80°–82° C.

| Analysis: | | | |
|---|---|---|---|
| Calculated for C$_{18}$H$_{16}$O$_2$N$_2$: | C 73.9; | H 5.5; | N 9.6% |
| Found: | C 73.5; | H 5.5; | N 9.7% |

EXAMPLE 47

Preparation of 2-(3-phenoxybenzoyl)-3-dimethylaminoacrylonitrile

A mixture of 3-phenoxybenzoyl chloride (6.9 g), 3-dimethylaminoacrylonitrile (2 g) and triethylamine (4 g) in dry dioxan (50 ml) was refluxed for 6 hours under a nitrogen atmosphere. After standing at room temperature overnight, the dioxan was evaporated in vacuo and dichloromethane added to the residue. The extracts were washed with water, 2N NaOH, brine and finally dried over MgSO$_4$. After filtration and evaporation of the dichloromethane, the residue was purified on a silica gel column using 5% methanol-dichloromethane as eluant to give the title compound (2.2 g, 36%) as a white solid of m.p. 80°–82° C. (identical to that described in Example 46).

EXAMPLE 48

Preparation of 2-3-(5'-α, α, α-trifluoromethyl-2-pyridyloxy)benzoyl]-3-dimethylaminoacrylonitrile Dimethylformamide-dimethyl acetal (3 ml) was added to a solution of 3-(5'-α, α, α-trifluoromethyl-2-pyridyloxy)benzoyl acetonitrile (1g) in dichlormethane (50 ml). After stirring at room temperature overnight, the methylene chloride was evaporated and the residual oil chromatographed on a silica gel column using 5% methanol-dichloromethane (v/v) as eluant to give the title product (0.9 g, 85%) as a viscous colourless oil.

| Analysis: | | | |
|---|---|---|---|
| Calculated for C$_{18}$H$_{14}$N$_3$O$_2$F$_3$: | C 59.8; | H 3.8; | N 11.6% |
| Found: | C 57.8; | H 3.7; | N 11.2% |

The compounds of general formula I listed in Table 2, were prepared by methods similar to those described in Examples 45 to 48 above.

TABLE 2

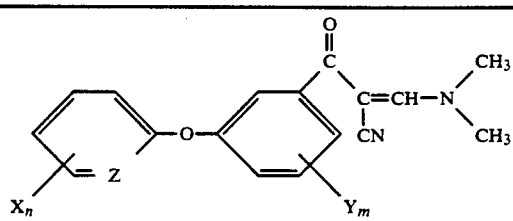

| Example No. | Xn | Z | Ym | C (Calc. Found) | H (Calc. Found) | N (Calc. Found) | Melting Point (°C.) |
|---|---|---|---|---|---|---|---|
| 49 | 2-Cl, 4-CF$_3$ | CH | — | 57.8 / 57.4 | 3.5 / 3.5 | 7.1 / 6.9 | 68–70 |
| 50 | 4-Cl | CH | — | 66.3 / 66.4 | 4.6 / 4.6 | 8.6 / 8.6 | 101–102 |
| 51 | 4-CH$_3$ | CH | — | 74.5 / 74.4 | 5.9 / 6.0 | 9.2 / 9.4 | 120–121 |
| 52 | 3,5-diCl | CH | — | 59.6 / 58.8 | 3.9 / 4.5 | 7.7 / 7.6 | 101–102 |
| 53 | 4-OCH$_3$ | CH | — | 70.8 / 70.7 | 5.6 / 5.7 | 8.7 / 8.8 | 117–118 |
| 54 | 3,4-diCl | CH | — | 59.6 / 60.6 | 3.9 / 4.1 | 7.7 / 8.0 | 102–103 |
| 55 | 4-isopropyl | CH | — | 75.5 / 74.3 | 6.6 / 6.6 | 8.4 / 8.5 | 81–83 |
| 56 | 2,4-diCH$_3$ | CH | — | 75.0 / 74.1 | 6.3 / 6.2 | 8.8 / 8.6 | 120—121 |
| 57 | 5-Cl | N | — | 62.4 / 62.5 | 4.3 / 4.9 | 12.8 / 12.9 | 119–120 |
| 58 | 2-CH$_3$ | CH | — | 74.5 / 71.5 | 5.9 / 5.8 | 9.2 / 8.9 | 79–81 |
| 59 | 4-SCH$_3$ | CH | — | 67.5 / 67.3 | 5.3 / 5.3 | 8.3 / 8.3 | 88–90 |
| 60 | 2,4-diCl | CH | — | 60.0 / 60.8 | 3.9 / 4.1 | 7.8 / 7.7 | 88–90 |
| 61 | 4-F | CH | — | 69.7 / 67.8 | 4.8 / 5.0 | 9.0 / 9.0 | oil |
| 62 | 3,4-diF | CH | — | 65.8 / 60.3 | 4.3 / 4.2 | 8.5 / 7.9 | oil |
| 63 | 2,5-diCH$_3$ | CH | — | 75.0 / 74.0 | 6.3 / 6.6 | 8.7 / 8.4 | oil |
| 64 | 2-F | CH | — | 69.7 / 68.6 | 4.8 / 4.5 | 9.0 / 9.1 | oil |
| 65 | 3-F | CH | — | 69.7 / 63.7 | 4.8 / 4.6 | 9.0 / 8.7 | oil |
| 66 | 4-CN | CH | — | 71.9 / 71.2 | 4.7 / 4.7 | 13.2 / 13.3 | 121–122 |
| 67 | 3-Cl | N | — | 62.3 / 62.1 | 4.3 / 4.3 | 12.8 / 12.8 | oil |
| 68 | 5-Br | N | — | 54.8 / 54.6 | 3.7 / 3.8 | 11.3 / 11.0 | 120–122 |
| 69 | 3-CF$_3$, 4-Cl | CH | — | 57.9 / 56.9 | 3.6 / 3.7 | 7.1 / 7.0 | 92–94 |
| 70 | 4-C$_2$H$_5$ | CH | — | 75.0 / 73.7 | 6.3 / 6.3 | 8.8 / 8.8 | 93–95 |
| 71 | 4-Br | CH | — | 58.2 / 57.9 | 4.0 / 4.1 | 7.5 / 7.7 | 111–113 |
| 72 | 4-tC$_4$H$_9$ | CH | — | 75.9 / 75.8 | 6.9 / 7.1 | 8.1 / 8.0 | 94–96 |
| 73 | 4-secC$_4$H$_9$ | CH | — | 75.9 / 78.3 | 6.9 / 7.6 | 8.1 / 7.6 | oil |
| 74 | 2-CH$_3$, 4-Cl | CH | — | 67.1 / 66.1 | 5.0 / 5.0 | 8.2 / 8.2 | 120–122 |
| 75 | 3-CF$_3$, 4-F | CH | — | 60.3 / 58.4 | 3.7 / 4.0 | 7.4 / 7.2 | oil |
| 76 | 2-Cl | CH | — | 66.3 / 67.5 | 4.6 / 4.8 | 8.6 / 8.4 | 72–74 |
| 77 | 3-CH$_3$, 4-Cl | CH | — | 67.1 / 67.0 | 5.0 / 5.0 | 8.3 / 8.2 | 108–109 |
| 78 | 3-Cl | CH | — | 66.3 / 66.9 | 4.6 / 4.8 | 8.6 / 8.5 | oil |
| 79 | 3-OCH$_3$ | CH | — | 70.8 / 69.5 | 5.6 / 5.6 | 8.7 / 8.7 | oil |
| 80 | 2,4-diF | CH | — | 65.8 / 66.3 | 4.3 / 4.4 | 8.5 / 8.5 | 36–40 |
| 81 | 2-Cl, 4-F | CH | — | 62.8 / 64.5 | 4.1 / 4.2 | 8.1 / 8.3 | 103–105 |
| 82 | 3,5-diCH$_3$ | CH | — | 75.0 | 6.2 | 8.7 | 69–70 |

TABLE 2-continued

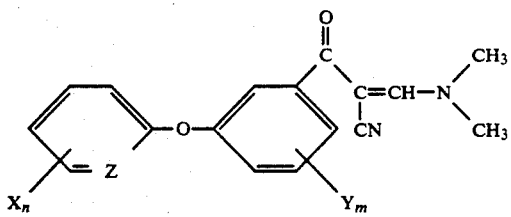

| Example No. | Xn | Z | Ym | C (Calc. Found) | H (Calc. Found) | N (Calc. Found) | Melting Point (°C.) |
|---|---|---|---|---|---|---|---|
| 83 | 3-CF$_3$ | CH | 5-Cl | 74.3 57.8 55.5 | 6.4 3.5 3.3 | 8.7 7.1 7.0 | oil |
| 84 | 3-CH$_2$CN, 5-CF$_3$ | N | — | 60.0 58.4 | 3.7 4.1 | 14.0 13.0 | 65–67 |

EXAMPLE 85

Preparation of 2-[3-(4'-methylsulphinylphenoxy)-benzoyl]-3-dimethylaminoacrylonitrile A mixture of 2-[3-(4'-methylmercaptophenoxy)-benzoyl]-3-dimethylaminoacrylonitrile (2 g, from Example 59) and meta-chloroperoxybenzoic acid (1.2 g) in methylene chloride (50 ml) was stirred at room temperature overnight. The mixture was then washed with 10% aqueous sodium hydroxide, dried over magnesium sulphate and evaporated. The residual solid was chromatographed on a silica gel column using methanol as eluant to give the title compound (1.6 g) as a white solid of m.p.

| Analysis: | | | |
|---|---|---|---|
| Calculated for C$_{19}$H$_{18}$O$_3$N$_2$S: | C 64.4; | H 5.1; | N 7.9% |
| Found: | C 64.0; | H 5.1; | N 7.9% |

EXAMPLE 86

Preparation of 2-[3-(4'-methylsulphonylphenoxy)-benzoyl]-3-dimethylaminoacrylonitrile A mixture of 2-[3-(4'-methylmercaptophenoxy)benzoyl]-3-dimethylaminoacrylonitrile (2.5 g, from Example 59) and meta-chloroperoxybenzoic acid (2.9 g) in methylene chloride (50 ml) was stirred at room temperature for 3 hours. The mixture was then filtered and the methylene chloride evaporated. The residual solid was chromatographed on a silica-gel column using 20% (v/v) diethyl ether-methylene chloride as eluant to give the title compuond (1.3 g) as a white solid of m.p. 45°–50° C.

| Analysis: | | | |
|---|---|---|---|
| Calculated for C$_{19}$H$_{18}$O$_4$N$_2$S: | C 61.6; | H 4.9; | N 7.6% |
| Found: | C 58.9; | H 5.0; | N 7.4% |

EXAMPLE 87

Preparation of 3-(4'-nitrophenoxy)benzoyl]-3-dimethylaminoacrylonitrile

A mixture of anhydrous potassium carbonate (1.3 g), p-fluoronitrobenzene (1.5 g) and 2-(3'-hydroxybenzoyl)-3-dimethylaminoacrylonitrile (2.1 g) in dry dimethylformamide (50 ml) was stirred and refluxed for 3 hours. After cooling, the mixture was poured into water (100 ml) and the aqueous solution extracted with diethyl ether. After drying the diethyl ether extracts over anhydrous magnesium sulphate, the solvent was evaporated off and the residue chromatographed on a silica gel column using 10% diethyl ether-dichloromethane (v/v) as eluant to give the title compound (1.8 g) as a pale yellow solid of m.p. 117°–118° C.

| Analysis: | | | |
|---|---|---|---|
| Calculated for C$_{18}$H$_{15}$N$_3$O$_4$: | C 64.1; | H 4.4; | N 12.5% |
| Found: | C 63.7; | H 4.5; | N 12.3% |

The compounds of general formula I listed in Table 3 below, were prepared by methods similar to those described in Example 87 above.

TABLE 3

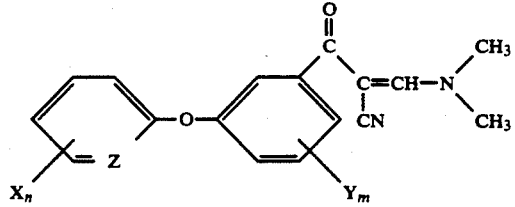

| Example No. | Xn | Z | Ym | C (Calc. Found) | H (Calc. Found) | N (Calc. Found) | Melting Point (°C.) |
|---|---|---|---|---|---|---|---|
| 88 | 2-NO$_2$, 4-Cl | CH | — | 58.2 58.3 | 3.8 3.9 | 11.3 11.7 | 114–115 |
| 89 | 2-NO$_2$, 4-Br | CH | — | 52.0 52.6 | 3.4 3.7 | 10.1 10.0 | oil |
| 90 | 3-Cl, 5-CF$_3$ | N | — | 54.6 54.4 | 3.3 3.4 | 10.6 10.6 | 146–147 |
| 91 | 5-CF$_3$, | N | — | 54.6 | 3.3 | 10.6 | 50–52 |

TABLE 3-continued

| | | | | Elemental Analysis (%) | | | |
|---|---|---|---|---|---|---|---|
| Example No. | Xn | Z | Ym | C (Calc. Found) | H (Calc. Found) | N (Calc. Found) | Melting Point (°C.) |
| | 6-Cl | | | 54.5 | 3.4 | 10.3 | |

EXAMPLE 92

Herbicidal Activity

To evaluate their herbicidal activity, compounds according to the invention were tested using as representative range of plants: maize, *Zea mays* (Mz); rice, *Oryza sativa* (R); barnyard grass, *Echinochloa crusgalli* (BG); oat, *Avena sativa* (O); linseed, *Linum usitatissimum* (L); mustard, *Sinapsis alba* (M); sugar beet, *Beta vulgaris* (SB) and soya bean, *Glycine max* (S).

The tests fall into two categories, pre-emergence and post-emergence. The pre-emergence tests involved spraying a liquid formulation of the compound onto the soil in which the seeds of the plant species mentioned above had recently been sown. The post-emergence tests involved two types of test, viz., soil drench and foliar spray tests. In the soil drench tests the soil in which the seedling plants of the above species were growing was drenched with a liquid formulation containing a compound of the invention, and in the foliar spray tests the seedling plants were sprayed with such a formulation.

The soil used in the tests was a prepared horticultural loam.

The formulations used in the tests were prepared from solutions of the test compounds in acetone containing 0.4% by weight of an alkylphenol/ethylene oxide condensate available under the trade mark TRITON X-155. These acetone solutions were diluted with water and the resulting formulations applied at dosage levels corresponding to 5 kg or 1 kg of active material per hectare in a volume equivalent to 600 litres per hectare in the soil spray and foliar spray test, and at a dosage of level equivalent to 10 kilograms of active material per hectare in a volume equivalent to approximately 3,000 litres per hectare in the soil drench tests.

In the pre-emergence tests untreated sown soil and in the post-emergence tests untreated soil bearing seedling plants were used as controls.

The herbicidal effects of the test compounds were assessed visually twelve days after spraying the foliage and the soil, and thirteen days after drenching the soil and were recorded on a 0-9 scale. A rating 0 indicates growth as untreated control, a rating 9 indicates death. An increase of 1 unit on the linear scale approximates to a 10% increase in the level of effect.

The results of the tests are set out in Table 4 below. There are included in Table 4 for comparison purposes the following acrylonitrile derivatives described in German OLS 2330913:

| Compound A | 2-benzoyl-3-dimethylaminoacrylonitrile |
|---|---|
| Compound B | 2-(3-methoxybenzoyl)-3-dimethylamino-acrylonitrile) |

TABLE 4

| Compound of Ex. No. | Soil drench 10/kg/ha | | | | | | | | Dosage kg/ha | Foliar spray | | | | | | | | Pre-emergence | | | | | | | |
|---|---|---|---|---|---|---|---|---|---|---|---|---|---|---|---|---|---|---|---|---|---|---|---|---|---|
| | Mz | R | BG | O | L | M | SB | S | | Mz | R | BG | O | L | M | SB | S | Mz | R | BG | O | L | M | SB | S |
| Compound A | 6 | 3 | 6 | 5 | 5 | 6 | 5 | 7 | 5 | 3 | 1 | 5 | 2 | 4 | 5 | 6 | 5 | 6 | 4 | 8 | 6 | 5 | 6 | 7 | 5 |
| | | | | | | | | | 1 | 0 | 0 | 1 | 0 | 3 | 3 | 3 | 3 | 2 | 0 | 3 | 1 | 2 | 3 | 6 | 0 |
| Compound B | 6 | 5 | 6 | 6 | 6 | 8 | 8 | 8 | 5 | 4 | 0 | 5 | 0 | 5 | 8 | 7 | 5 | 7 | 6 | 9 | 7 | 7 | 9 | 9 | 6 |
| | | | | | | | | | 1 | 0 | 0 | 1 | 0 | 3 | 5 | 6 | 3 | 4 | 0 | 1 | 2 | 1 | 4 | 4 | 2 |
| 45 | 4 | 3 | 6 | 6 | 2 | 3 | 4 | 0 | 5 | 7 | 3 | 9 | 7 | 8 | 9 | 9 | 6 | 2 | 3 | 4 | 5 | 4 | 8 | 8 | 0 |
| | | | | | | | | | 1 | 4 | 2 | 7 | 5 | 7 | 9 | 9 | 5 | 1 | 1 | 2 | 4 | 3 | 6 | 6 | 0 |
| 46 | 7 | 7 | 7 | 6 | 6 | 6 | 7 | 1 | 5 | 5 | 4 | 8 | 3 | 6 | 7 | 8 | 6 | 5 | 4 | 9 | 5 | 5 | 9 | 9 | 1 |
| | | | | | | | | | 1 | 3 | 2 | 7 | 2 | 6 | 7 | 7 | 5 | 5 | 4 | 8 | 4 | 3 | 8 | 8 | 1 |
| 48 | 8 | 8 | 8 | 9 | 8 | 9 | 9 | 7 | 5 | 5 | 4 | 8 | 8 | 8 | 9 | 7 | 7 | 8 | 6 | 8 | 7 | 8 | 9 | 9 | 3 |
| | | | | | | | | | 1 | 2 | 0 | 6 | 3 | 6 | 7 | 8 | 6 | 6 | 3 | 7 | 6 | 3 | 7 | 9 | 0 |
| 49 | 4 | 4 | 6 | 6 | 1 | 3 | 4 | 0 | 5 | 6 | 3 | 8 | 5 | 9 | 8 | 8 | 7 | 2 | 1 | 8 | 5 | 8 | 9 | 9 | 7 |
| | | | | | | | | | 1 | 4 | 1 | 7 | 3 | 7 | 8 | 8 | 6 | 1 | 0 | 7 | 2 | 5 | 9 | 8 | 3 |
| 50 | 5 | 4 | 6 | 5 | 2 | 4 | 4 | 2 | 5 | 6 | 5 | 8 | 7 | 6 | 9 | 9 | 6 | 3 | 4 | 5 | 5 | 3 | 8 | 8 | 2 |
| | | | | | | | | | 1 | 3 | 2 | 7 | 4 | 6 | 9 | 9 | 6 | 1 | 1 | 3 | 3 | 1 | 6 | 7 | 2 |
| 51 | 4 | 5 | 6 | 5 | 4 | 3 | 3 | 3 | 5 | 6 | 4 | 8 | 6 | 7 | 8 | 7 | 7 | 1 | 4 | 2 | 4 | 3 | 6 | 1 | 0 |
| | | | | | | | | | 1 | 5 | 3 | 8 | 5 | 7 | 7 | 6 | 7 | 0 | 0 | 0 | 3 | 1 | 4 | 0 | 0 |
| 52 | 3 | 1 | 5 | 4 | 2 | 2 | 3 | 0 | 5 | 4 | 3 | 8 | 7 | 8 | 9 | 9 | 7 | 0 | 0 | 2 | 1 | 3 | 5 | 6 | 0 |
| | | | | | | | | | 1 | 3 | 1 | 7 | 5 | 7 | 9 | 8 | 5 | 0 | 0 | 0 | 0 | 1 | 4 | 3 | 0 |
| 53 | 5 | 5 | 5 | 6 | 5 | 4 | 4 | 2 | 5 | 6 | 4 | 8 | 7 | 7 | 8 | 8 | 7 | 4 | 5 | 5 | 5 | 2 | 5 | 4 | 0 |
| | | | | | | | | | 1 | 4 | 3 | 7 | 4 | 6 | 8 | 7 | 7 | 1 | 3 | 4 | 3 | 2 | 3 | 2 | 0 |
| 54 | 2 | 0 | 5 | 5 | 0 | 0 | 0 | 0 | 5 | 5 | 3 | 8 | 8 | 9 | 9 | 7 | 0 | 0 | 0 | 0 | 0 | 2 | 3 | 4 | 0 |
| | | | | | | | | | 1 | 4 | 2 | 7 | 4 | 7 | 9 | 9 | 6 | 0 | 0 | 0 | 0 | 1 | 3 | 3 | 0 |
| 55 | 5 | 0 | 4 | 4 | 0 | 3 | 0 | 2 | 5 | 6 | 1 | 8 | 4 | 7 | 9 | 7 | 5 | 0 | 0 | 5 | 2 | 4 | 8 | 4 | 0 |
| | | | | | | | | | 1 | 4 | 1 | 6 | 2 | 6 | 8 | 5 | 4 | 0 | 0 | 5 | 1 | 3 | 7 | 3 | 0 |
| 56 | 4 | 4 | 6 | 5 | 1 | 0 | 3 | 2 | 5 | 5 | 2 | 7 | 3 | 7 | 7 | 8 | 6 | 0 | 0 | 3 | 3 | 4 | 6 | 4 | 2 |
| | | | | | | | | | 1 | 4 | 2 | 6 | 3 | 5 | 6 | 6 | 5 | 0 | 0 | 1 | 1 | 2 | 6 | 2 | 1 |
| 57 | 7 | 5 | 8 | 7 | 4 | 9 | 9 | 4 | 5 | 4 | 0 | 9 | 5 | 7 | 9 | 9 | 6 | 6 | 4 | 8 | 7 | 3 | 8 | 9 | 0 |
| | | | | | | | | | 1 | 3 | 0 | 9 | 4 | 6 | 9 | 8 | 5 | 5 | 2 | 7 | 4 | 1 | 4 | 8 | 0 |
| 58 | 5 | 4 | 6 | 5 | 4 | 5 | 2 | 0 | 5 | 5 | 4 | 8 | 5 | 7 | 9 | 9 | 6 | 4 | 3 | 8 | 5 | 7 | 8 | 8 | 4 |
| | | | | | | | | | 1 | 4 | 2 | 6 | 3 | 6 | 8 | 9 | 5 | 2 | 3 | 7 | 3 | 4 | 8 | 5 | 0 |

TABLE 4-continued

| Compound of Ex. No. | Soil drench 10/kg/ha | | | | | | | | Dosage kg/ha | Foliar spray | | | | | | | | Pre-emergence | | | | | | | |
|---|---|---|---|---|---|---|---|---|---|---|---|---|---|---|---|---|---|---|---|---|---|---|---|---|---|
| | Mz | R | BG | O | L | M | SB | S | | Mz | R | BG | O | L | M | SB | S | Mz | R | BG | O | L | M | SB | S |
| 59 | 2 | 0 | 4 | 6 | 1 | 4 | 6 | 0 | 5 | 3 | 2 | 7 | 3 | 5 | 8 | 6 | 4 | 0 | 0 | 2 | 3 | 4 | 7 | 7 | 0 |
|   |   |   |   |   |   |   |   |   | 1 | 2 | 0 | 6 | 2 | 4 | 6 | 6 | 2 | 0 | 0 | 1 | 1 | 2 | 7 | 6 | 0 |
| 85 | 4 | 1 | 2 | 5 | 0 | 6 | 4 | 0 | 5 | 3 | 2 | 6 | 4 | 4 | 7 | 7 | 4 | 0 | 0 | 3 | 4 | 3 | 8 | 8 | 0 |
|   |   |   |   |   |   |   |   |   | 1 | 1 | 1 | 6 | 3 | 4 | 7 | 7 | 3 | 0 | 0 | 1 | 1 | 2 | 6 | 6 | 0 |
| 86 | 5 | 2 | 4 | 5 | 0 | 4 | 4 | 0 | 5 | 2 | 0 | 7 | 3 | 4 | 7 | 7 | 3 | 3 | 0 | 3 | 3 | 2 | 6 | 5 | 0 |
|   |   |   |   |   |   |   |   |   | 1 | 0 | 0 | 3 | 0 | 2 | 6 | 5 | 2 | 0 | 0 | 0 | 0 | 1 | 3 | 3 | 0 |
| 60 | 2 | 4 | 4 | 4 | 2 | 2 | 4 | 2 | 5 | 4 | 4 | 7 | 5 | 6 | 9 | 8 | 5 | 0 | 0 | 5 | 2 | 4 | 7 | 8 | 2 |
|   |   |   |   |   |   |   |   |   | 1 | 3 | 3 | 7 | 4 | 6 | 8 | 7 | 4 | 0 | 0 | 4 | 2 | 3 | 7 | 8 | 1 |
| 61 | 6 | 5 | 7 | 7 | 5 | 8 | 9 | 4 | 5 | 7 | 3 | 8 | 6 | 7 | 9 | 9 | 7 | 5 | 5 | 8 | 7 | 5 | 8 | 9 | 2 |
|   |   |   |   |   |   |   |   |   | 1 | 4 | 1 | 7 | 4 | 5 | 9 | 9 | 6 | 4 | 3 | 7 | 5 | 3 | 7 | 8 | 0 |
| 62 | 6 | 5 | 6 | 6 | 4 | 6 | 9 | 4 | 5 | 7 | 2 | 8 | 7 | 7 | 9 | 9 | 7 | 4 | 4 | 7 | 6 | 7 | 8 | 9 | 1 |
|   |   |   |   |   |   |   |   |   | 1 | 4 | 1 | 7 | 4 | 5 | 8 | 8 | 6 | 2 | 2 | 6 | 5 | 2 | 4 | 8 | 0 |
| 63 | 5 | 4 | 5 | 5 | 3 | 4 | 5 | 2 | 5 | 4 | 1 | 6 | 5 | 6 | 8 | 8 | 6 | 3 | 2 | 5 | 4 | 4 | 7 | 8 | 2 |
|   |   |   |   |   |   |   |   |   | 1 | 4 | 0 | 4 | 3 | 4 | 7 | 8 | 5 | 1 | 0 | 4 | 2 | 2 | 5 | 8 | 0 |
| 64 | 5 | 4 | 6 | 5 | 5 | 9 | 4 | 4 | 5 | 4 | 2 | 8 | 5 | 7 | 9 | 9 | 6 | 4 | 4 | 6 | 7 | 6 | 8 | 9 | 1 |
|   |   |   |   |   |   |   |   |   | 1 | 3 | 1 | 6 | 2 | 6 | 8 | 9 | 6 | 4 | 2 | 6 | 3 | 2 | 7 | 5 | 0 |
| 65 | 6 | 6 | 7 | 6 | 6 | 9 | 9 | 3 | 5 | 4 | 2 | 9 | 5 | 7 | 9 | 9 | 6 | 6 | 6 | 8 | 7 | 7 | 8 | 9 | 2 |
|   |   |   |   |   |   |   |   |   | 1 | 2 | 0 | 7 | 4 | 5 | 9 | 9 | 5 | 5 | 4 | 6 | 5 | 4 | 6 | 8 | 0 |
| 66 | 6 | 2 | 6 | 7 | 4 | 5 | 9 | 2 | 5 | 5 | 1 | 6 | 6 | 7 | 8 | 9 | 6 | 5 | 2 | 7 | 7 | 4 | 4 | 9 | 2 |
|   |   |   |   |   |   |   |   |   | 1 | 2 | 0 | 3 | 1 | 3 | 8 | 8 | 4 | 4 | 0 | 5 | 2 | 1 | 1 | 8 | 0 |
| 67 | 5 | 4 | 6 | 5 | 5 | 7 | 4 | 0 | 5 | 4 | 0 | 5 | 2 | 6 | 7 | 5 | 5 | 4 | 3 | 5 | 5 | 3 | 5 | 7 | 0 |
|   |   |   |   |   |   |   |   |   | 1 | 2 | 0 | 1 | 0 | 4 | 5 | 4 | 5 | 3 | 0 | 3 | 2 | 1 | 3 | 4 | 0 |
| 68 | 6 | 6 | 7 | 7 | 5 | 7 | 7 | 3 | 5 | 5 | 3 | 8 | 5 | 6 | 9 | 8 | 6 | 4 | 4 | 7 | 5 | 4 | 8 | 8 | 0 |
|   |   |   |   |   |   |   |   |   | 1 | 2 | 1 | 7 | 3 | 5 | 7 | 5 | 4 | 1 | 1 | 4 | 4 | 2 | 7 | 7 | 0 |
| 69 | 2 | 0 | 4 | 4 | 3 | 4 | 6 | 2 | 5 | 5 | 2 | 9 | 5 | 8 | 9 | 9 | 8 | 0 | 0 | 0 | 1 | 2 | 5 | 5 | 0 |
|   |   |   |   |   |   |   |   |   | 1 | 3 | 1 | 6 | 3 | 8 | 9 | 9 | 7 | 0 | 0 | 0 | 0 | 1 | 2 | 3 | 0 |
| 70 | 7 | 4 | 7 | 7 | 4 | 5 | 3 | 2 | 5 | 5 | 2 | 8 | 5 | 7 | 9 | 8 | 7 | 0 | 0 | 3 | 3 | 3 | 5 | 4 | 0 |
|   |   |   |   |   |   |   |   |   | 1 | 3 | 1 | 6 | 3 | 6 | 8 | 8 | 6 | 0 | 0 | 3 | 1 | 0 | 4 | 1 | 0 |
| 88 | 5 | 4 | 5 | 5 | 2 | 4 | 5 | 0 | 5 | 6 | 2 | 7 | 5 | 6 | 8 | 6 | 6 | 0 | 0 | 2 | 1 | 3 | 5 | 8 | 0 |
|   |   |   |   |   |   |   |   |   | 1 | 4 | 1 | 5 | 3 | 3 | 7 | 5 | 6 | 0 | 0 | 1 | 0 | 1 | 4 | 8 | 0 |
| 87 | 6 | 4 | 6 | 6 | 4 | 4 | 2 | 0 | 5 | 6 | 1 | 6 | 5 | 6 | 7 | 8 | 5 | 4 | 3 | 6 | 5 | 3 | 6 | 8 | 0 |
|   |   |   |   |   |   |   |   |   | 1 | 5 | 0 | 5 | 3 | 4 | 6 | 5 | 5 | 1 | 1 | 4 | 4 | 1 | 4 | 4 | 0 |
| 89 | 5 | 5 | 6 | 5 | 1 | 3 | 3 | 0 | 5 | 4 | 2 | 6 | 2 | 4 | 7 | 7 | 5 | 0 | 0 | 2 | 0 | 2 | 4 | 4 | 0 |
|   |   |   |   |   |   |   |   |   | 1 | 4 | 2 | 5 | 2 | 3 | 7 | 7 | 4 | 0 | 0 | 0 | 0 | 0 | 3 | 3 | 0 |
| 71 | 6 | 5 | 7 | 6 | 2 | 5 | 5 | 0 | 5 | 4 | 3 | 8 | 5 | 7 | 9 | 8 | 7 | 2 | 2 | 4 | 5 | 4 | 7 | 9 | 0 |
|   |   |   |   |   |   |   |   |   | 1 | 4 | 2 | 6 | 3 | 6 | 9 | 6 | 6 | 1 | 0 | 3 | 4 | 3 | 7 | 8 | 0 |
| 72 | 0 | 0 | 2 | 3 | 0 | 3 | 0 | 0 | 5 | 4 | 3 | 6 | 6 | 7 | 9 | 5 | 6 | 0 | 0 | 2 | 1 | 3 | 7 | 5 | 0 |
|   |   |   |   |   |   |   |   |   | 1 | 3 | 1 | 2 | 3 | 5 | 9 | 4 | 3 | 0 | 0 | 1 | 0 | 1 | 4 | 0 | 0 |
| 73 | 0 | 0 | 0 | 0 | 0 | 0 | 0 | 0 | 5 | 4 | 1 | 6 | 3 | 5 | 8 | 5 | 6 | 0 | 0 | 2 | 0 | 2 | 3 | 5 | 0 |
|   |   |   |   |   |   |   |   |   | 1 | 2 | 1 | 3 | 2 | 4 | 7 | 5 | 5 | 0 | 0 | 1 | 0 | 0 | 2 | 3 | 0 |
| 74 | 5 | 3 | 6 | 4 | 0 | 5 | 6 | 0 | 5 | 4 | 3 | 7 | 5 | 6 | 9 | 8 | 7 | 0 | 0 | 4 | 2 | 4 | 5 | 9 | 3 |
|   |   |   |   |   |   |   |   |   | 1 | 2 | 1 | 5 | 4 | 6 | 9 | 8 | 5 | 0 | 0 | 4 | 1 | 2 | 4 | 9 | 2 |
| 75 | 5 | 4 | 6 | 6 | 2 | 5 | 4 | 2 | 5 | 7 | 3 | 8 | 7 | 8 | 9 | 9 | 8 | 3 | 2 | 6 | 5 | 4 | 8 | 9 | 3 |
|   |   |   |   |   |   |   |   |   | 1 | 5 | 2 | 6 | 4 | 7 | 9 | 9 | 7 | 1 | 0 | 3 | 3 | 3 | 5 | 8 | 2 |
| 76 | 6 | 4 | 7 | 6 | 4 | 4 | 5 | 0 | 5 | 5 | 2 | 8 | 3 | 7 | 9 | 8 | 6 | 4 | 4 | 6 | 5 | 5 | 8 | 8 | 1 |
|   |   |   |   |   |   |   |   |   | 1 | 3 | 1 | 7 | 1 | 6 | 9 | 7 | 6 | 4 | 3 | 5 | 3 | 3 | 4 | 8 | 0 |
| 77 | 4 | 3 | 5 | 4 | 0 | 3 | 4 | 0 | 5 | 4 | 3 | 7 | 4 | 7 | 8 | 8 | 6 | 0 | 0 | 3 | 4 | 4 | 8 | 8 | 0 |
|   |   |   |   |   |   |   |   |   | 1 | 3 | 2 | 5 | 3 | 6 | 8 | 7 | 5 | 0 | 0 | 2 | 1 | 3 | 8 | 6 | 0 |
| 78 | 5 | 5 | 7 | 6 | 3 | 4 | 6 | 0 | 5 | 5 | 3 | 8 | 4 | 8 | 9 | 8 | 7 | 1 | 2 | 5 | 6 | 5 | 8 | 8 | 0 |
|   |   |   |   |   |   |   |   |   | 1 | 3 | 0 | 6 | 3 | 8 | 8 | 5 | 0 | 0 | 4 | 3 | 8 | 8 | 0 |   |   |
| 79 | 5 | 6 | 7 | 7 | 5 | 8 | 6 | 2 | 5 | 5 | 3 | 8 | 4 | 7 | 9 | 8 | 6 | 3 | 4 | 7 | 6 | 5 | 8 | 9 | 0 |
|   |   |   |   |   |   |   |   |   | 1 | 2 | 0 | 7 | 3 | 6 | 9 | 7 | 6 | 2 | 2 | 5 | 4 | 4 | 8 | 8 | 0 |
| 90 | 7 | 5 | 7 | 8 | 5 | 8 | 8 | 3 | 5 | 5 | 3 | 8 | 5 | 7 | 9 | 8 | 7 | 5 | 5 | 7 | 7 | 6 | 9 | 5 | 0 |
|   |   |   |   |   |   |   |   |   | 1 | 4 | 2 | 6 | 4 | 6 | 9 | 8 | 7 | 4 | 3 | 4 | 6 | 3 | 9 | 3 | 0 |
| 91 | 5 | 3 | 5 | 4 | 1 | 5 | 5 | 0 | 5 | 5 | 1 | 8 | 4 | 8 | 9 | 9 | 5 | 0 | 0 | 5 | 3 | 2 | 7 | 8 | 2 |
|   |   |   |   |   |   |   |   |   | 1 | 3 | 0 | 5 | 1 | 7 | 9 | 8 | 4 | 0 | 0 | 2 | 0 | 1 | 4 | 4 | 0 |
| 80 | 7 | 5 | 7 | 7 | 5 | 5 | 8 | 0 | 5 | 7 | 4 | 8 | 3 | 7 | 9 | 9 | 7 | 6 | 6 | 5 | 5 | 2 | 4 | 8 | 0 |
|   |   |   |   |   |   |   |   |   | 1 | 5 | 3 | 6 | 0 | 6 | 8 | 6 | 6 | 5 | 4 | 4 | 3 | 1 | 2 | 4 | 0 |
| 81 | 7 | 5 | 7 | 7 | 4 | 4 | 8 | 2 | 5 | 5 | 3 | 8 | 6 | 8 | 9 | 9 | 7 | 4 | 3 | 7 | 5 | 5 | 7 | 9 | 2 |
|   |   |   |   |   |   |   |   |   | 1 | 4 | 1 | 7 | 4 | 7 | 8 | 8 | 7 | 3 | 0 | 5 | 2 | 3 | 7 | 8 | 0 |
| 82 | 5 | 4 | 6 | 6 | 2 | 2 | 4 | 2 | 5 | 4 | 4 | 8 | 6 | 7 | 8 | 9 | 7 | 0 | 1 | 5 | 4 | 4 | 7 | 8 | 1 |
|   |   |   |   |   |   |   |   |   | 1 | 3 | 3 | 5 | 4 | 6 | 8 | 8 | 5 | 0 | 0 | 4 | 3 | 4 | 7 | 6 | 1 |
| 83 | 0 | 0 | 0 | 0 | 0 | 0 | 0 | 0 | 5 | 5 | 2 | 3 | 3 | 7 | 9 | 8 | 3 | 1 | 0 | 1 | 0 | 0 | 2 | 3 | 1 |
|   |   |   |   |   |   |   |   |   | 1 | 2 | 0 | 3 | 1 | 6 | 7 | 3 | 2 | 0 | 0 | 0 | 0 | 0 | 0 | 0 | 0 |
| 84 | 7 | 5 | 6 | 7 | 2 | 8 | 7 | 0 | 5 | 4 | 0 | 6 | 3 | 5 | 8 | 8 | 8 | 2 | 0 | 4 | 2 | 3 | 6 | 9 | 3 |
|   |   |   |   |   |   |   |   |   | 1 | 3 | 0 | 2 | 1 | 2 | 7 | 7 | 4 | 0 | 0 | 0 | 0 | 2 | 3 | 2 | 0 |

We claim:

1. A compound of the general formula I

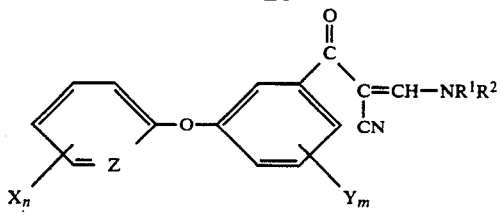

(I)

in which $R^1$ and $R^2$ each independently represents an alkyl group having from 1 to 6 carbon atoms, Z represents a nitrogen atom, m is 0 or 1, the Y or each Y independently represents a halogen atom, n is 0, 1 or 2, and the X or each X independently represents a halogen atom or a group selected from alkyl, haloalkyl, cyanoalkyl, alkenyl, alkynyl, alkenyloxy, alkynyloxy, alkoxy, alkylthio, alkenylthio, alkynylthio, cyano, nitro, alkylsulphonyl, alkylsulphinyl and sulphonamido wherein moieties have from 1 to 6 carbon atoms and alkenyl and alkynyl moieties have from 2 to 6 carbon atoms.

2. A compound as claimed in claim 1, wherein $R^1$ and $R^2$ are the same and each represents a methyl group.

3. A compound as claimed in claim 2 wherein m is 1 and Y represents a chlorine atom, or m is 0.

4. A compound as claimed in claim 2 wherein n is 1 or 2.

5. A compound as claimed in claim 4, wherein the X or each X is independently selected from halogen atoms, $C_{1-6}$ alkyl groups, $C_{1-6}$ haloalkyl groups, $C_{1-6}$ cyanolakyl groups, $C_{1-6}$ alkoxy groups, $C_{1-6}$ alkylthio groups, $C_{1-6}$ alkylsulphinyl groups, $C_{1-6}$ alkylsulphonyl groups, cyano groups and nitro groups.

6. A compound as claimed in claim 5, wherein the X or each X is independently selected from fluorine, chlorine, and bromine atoms and $C_{1-4}$ alkyl, trifluoromethyl, cyanomethyl, methoxy, methylthio, methylsulphinyl, methylsulphonyl, cyano and nitro groups.

7. A compound as claimed in claim 1 wherein m is 1 and Y represents a chlorine atom, or m is 0.

8. A compound as claimed in claim 1 wherein n is 1 or 2.

9. A compound as claimed in claim 1, wherein the X or each X is independently selected from halogen atoms, $C_{1-6}$ alkyl groups, $C_{1-6}$ haloalkyl groups, $C_{1-6}$ cyanolakyl groups, $C_{1-6}$ alkoxy groups, $C_{1-6}$ alkylsulphinyl groups, $C_{1-6}$ alkylsulphonyl groups, cyano groups and nitro groups.

10. A compound as claimed in claim 9, wherein the X or each X is independently selected from fluorine, chlorine, and bromine atoms and $C_{1-4}$ alkyl, trifluoromethyl, cyanomethyl, methoxy, methylthio, methylsulphinyl, methylsulphonyl, cyano and nitro groups.

11. A herbicidal composition which comprises an effective amount of a compound as claimed in claim 1 together with at least one inert carrier.

12. A composition as claimed in claim 11, comprising at least two inert carriers, at least one of which is a surface-active agent.

13. A method of combating undesired plant growth at a locus, which comprises treating the locus with an effective amount of a compound as claimed in claim 1.

14. A method of combating undesired plant growth at a locus, which comprises treating the locus with an effective amount of a composition as claimed in claim 11.

* * * * *

UNITED STATES PATENT AND TRADEMARK OFFICE
CERTIFICATE OF CORRECTION

PATENT NO. : 5,152,825

DATED : October 6, 1992

INVENTOR(S) : TERENCE GILKERSON ET AL

It is certified that error appears in the above-identified patent and that said Letters Patent is hereby corrected as shown below:

Claim 1 (column 23, line 19), before "moieties" insert -- alkyl --.

Signed and Sealed this

Twenty-first Day of September, 1993

Attest:

BRUCE LEHMAN

*Attesting Officer*  *Commissioner of Patents and Trademarks*